(12) United States Patent  
Schroeder (10) Patent No.: US 6,682,567 B1
(45) Date of Patent: Jan. 27, 2004

(54) METHOD AND APPARATUS FOR PROVIDING A SHELL COMPONENT INCORPORATING A POROUS INGROWTH MATERIAL AND LINER

(75) Inventor: David Wayne Schroeder, Winona Lake, IN (US)

(73) Assignee: Biomet, Inc., Warsaw, IN (US)

( * ) Notice: Subject to any disclaimer, the term of this patent is extended or adjusted under 35 U.S.C. 154(b) by 61 days.

(21) Appl. No.: 09/955,887

(22) Filed: Sep. 19, 2001

(51) Int. Cl.[7] .............................. A61F 2/32; A61B 17/58
(52) U.S. Cl. ........................ 623/22.24; 606/91; 606/99
(58) Field of Search ........................... 606/81, 91, 99; 623/22.23, 22.24, 22.28, 22.33, 22.35, 22.37, 22.38

(56) References Cited

U.S. PATENT DOCUMENTS

| | | |
|---|---|---|
| 3,605,123 A | 9/1971 | Hahn |
| 3,808,606 A | 5/1974 | Tronzo |
| 3,986,212 A | 10/1976 | Sauer |
| 4,051,559 A | 10/1977 | Pifferi |
| 4,164,794 A | 8/1979 | Spector et al. |
| 4,168,326 A * | 9/1979 | Broemer et al. ............ 427/2.24 |
| 4,184,213 A | 1/1980 | Heimke |
| 4,205,400 A | 6/1980 | Shen et al. |
| 4,217,666 A | 8/1980 | Averill |
| 4,234,972 A | 11/1980 | Hench et al. |
| 4,285,070 A | 8/1981 | Averill |
| 4,307,472 A | 12/1981 | Morris |
| 4,330,891 A | 5/1982 | Branemark et al. |
| 4,351,069 A | 9/1982 | Ballintyn et al. |
| 4,355,428 A | 10/1982 | Deloison et al. |
| 4,362,681 A | 12/1982 | Spector et al. |
| 4,479,271 A | 10/1984 | Bolesky et al. |
| 4,563,778 A | 1/1986 | Roche et al. |
| 4,566,138 A * | 1/1986 | Lewis et al. ............. 623/22.38 |
| 4,666,450 A | 5/1987 | Kenna |
| 4,685,923 A | 8/1987 | Mathys |
| 4,715,860 A * | 12/1987 | Amstutz et al. .......... 623/22.33 |
| 4,756,862 A | 7/1988 | Spector et al. |
| 4,769,041 A | 9/1988 | Morscher |
| 4,778,474 A | 10/1988 | Homsy |

(List continued on next page.)

FOREIGN PATENT DOCUMENTS

| | | |
|---|---|---|
| CH | 572 335 | 11/1974 |
| DE | 23 49 357 A1 | 4/1975 |
| DE | 24 11 617 A1 | 4/1975 |
| DE | 27 51 537 A1 | 5/1979 |
| DE | 28 05 868 A1 | 8/1979 |
| DE | 31 30 732 A1 | 5/1983 |
| EP | 0 010 527 | 4/1980 |
| EP | 0 053 794 | 6/1982 |
| FR | 2 395 011 | 1/1979 |
| FR | 2 639 218 | 5/1990 |
| FR | 2 685 192 | 6/1993 |
| FR | 2 698 782 | 6/1994 |

OTHER PUBLICATIONS

Dave Schroeder, One Piece Molded Shell With Porous Ingrowth Material, Jun. 28, 2000, Notebook No. 313, pp. 20–21, Disclosure No. BMT 4300 B–359.

*Primary Examiner*—Pedro Philogene
*Assistant Examiner*—David A. Bonderer
(74) *Attorney, Agent, or Firm*—Harness, Dickey & Pierce, P.L.C.

(57) ABSTRACT

An acetabular prosthesis including a ceramic shell having multiple layers and a polymer liner formed integrally with the shell. The acetabular prosthesis shell is formed of a ceramic wherein several layers with varying porosities and thicknesses are sintered together to form a unitary structure. A polymer inner liner forms a bearing within the shell to receive the ball of a femur or femur prosthesis. The polymer liner is formed in the ceramic shell and includes a plurality of portions which interdigitate into the pores of the inner porous layer of the ceramic shell.

38 Claims, 9 Drawing Sheets

U.S. PATENT DOCUMENTS

| | | |
|---|---|---|
| 4,813,960 A | 3/1989 | Muller |
| 4,840,630 A | 6/1989 | Kitamura |
| 4,883,492 A | 11/1989 | Frey et al. |
| 4,923,473 A | 5/1990 | Griss et al. |
| 4,963,154 A * | 10/1990 | Anapliotis et al. ....... 623/22.28 |
| 4,969,910 A | 11/1990 | Frey et al. |
| 4,978,355 A | 12/1990 | Frey et al. |
| 5,171,287 A | 12/1992 | Willert et al. |
| 5,236,457 A | 8/1993 | Devanathan |
| 5,263,988 A * | 11/1993 | Huebner ................ 623/22.29 |
| 5,282,861 A | 2/1994 | Kaplan |
| 5,290,315 A | 3/1994 | DeCarlo, Jr. |
| 5,336,265 A | 8/1994 | Serbousek et al. |
| 5,370,698 A | 12/1994 | Heimke et al. |
| 5,443,512 A | 8/1995 | Parr et al. |
| 5,443,519 A | 8/1995 | Averill et al. |
| 5,456,723 A | 10/1995 | Steinemann et al. |
| 5,549,698 A * | 8/1996 | Averill et al. ............ 623/22.22 |
| 5,549,700 A * | 8/1996 | Graham et al. .......... 623/22.14 |
| 5,658,338 A | 8/1997 | Tullos et al. |
| 5,658,345 A * | 8/1997 | Willi ...................... 623/22.26 |
| 5,662,158 A * | 9/1997 | Caldarise ................... 164/456 |
| 5,669,909 A | 9/1997 | Zdeblick et al. |
| 5,755,809 A | 5/1998 | Cohen et al. |
| 5,879,398 A | 3/1999 | Swarts et al. |
| 5,972,032 A * | 10/1999 | Lopez et al. ............. 623/22.32 |
| 6,022,357 A * | 2/2000 | Reu et al. ..................... 606/99 |
| 6,087,553 A | 7/2000 | Cohen et al. |
| 6,105,235 A | 8/2000 | Caldarise |
| 6,475,243 B1 * | 11/2002 | Sheldon et al. .......... 623/22.28 |

* cited by examiner

METHOD AND APPARATUS FOR PROVIDING A SHELL COMPONENT INCORPORATING A POROUS INGROWTH MATERIAL AND LINER

FIELD OF THE INVENTION

The present invention relates generally to a method and apparatus for use in orthopedic surgery and more particular to a method and apparatus for providing a shell component incorporating a porous ingrowth material and liner for use during an orthopedic surgical procedure, particularly with respect to a prosthetic hip.

BACKGROUND OF THE INVENTION

A natural hip joint may undergo degenerative changes due to a variety of etiologies. When these degenerative changes become so far advanced and irreversible, it may ultimately become necessary to replace a natural hip joint with a prosthetic hip. To replace the hip, a prosthetic hip may be affixed to the femur in one of many ways generally known in the art. In addition to replacing the femoral portion of the hip joint, the acetabulum portion of the hip joint may also require replacement. If the acetabulum also needs to be replaced or repaired, all the remnants of the articular cartilage are generally removed from the acetabulum and an acetabular prosthesis which will accommodate the head or ball of the hip prosthesis is affixed to the acetabulum. It is generally known in the art to affix the acetabular prosthesis to the acetabulum by means of cement, screws, or other appropriate fixation mechanisms.

A typical acetabular prosthesis generally includes two (2) modular portions. In particular, the modular portions include an acetabular cup or shell and a synthetic liner or bearing wherein the liner is affixed within the acetabular cup through a locking mechanism. The modular acetabular prosthesis allows for numerous liners to be produced for a singular acetabular cup or vice versa. Other modular attachments may include additional fixation mechanisms to affix the acetabular cup to the patient. This enables a surgeon performing the procedure to determine which would fit best for the particular patient. Although a modular acetabular prosthesis performs its job adequately, it would be desirable to have an acetabular prosthesis with an acetabular cup and a liner which does not allow any movement relative to each other once implanted into the bone.

If the acetabular cup and the liner move, such as by micromotion, wear material may result. This wear material may migrate out of the acetabular cup or may enter into the articulating area of the hip joint prosthesis. Over time, these foreign materials may cause additional wearing beyond what is desirable in the acetabular prosthesis. Because of the wear material, it may also be desirable to have an acetabular prosthesis that does not include bores through the acetabular cup. The bores, which generally accept screws or other fixation devices, also allow foreign material or body fluids into the acetabular cup and wear material out of the acetabular cup, which may cause additional or accelerated degeneration of the acetabular prosthesis.

Therefore, it is desirable to provide a substantially non-modular acetabular prosthesis, such as an acetabular prosthesis which improves upon existing modular acetabular prostheses and does not suffer from the above mentioned disadvantages.

SUMMARY OF THE INVENTION

In accordance with the teachings of the present invention, a method and apparatus for providing a substantially non-modular acetabular cup which may include additional modular or non-modular flanges for use in orthopedic surgery is disclosed. The shell portion of the acetabular cup may be formed from a ceramic material that includes three integrally formed regions. In particular, a ceramic shell having an inner and outer porous region and therebetween a non-porous region. A liner may then be interdigitated into the inner porous region of the shell to be held firmly in place. The acetabular prosthesis is then placed into the bone of the ileum and the outer porous region allows bone to regrow to hold the acetabular prosthesis in place. When the shell is made of ceramic, the ceramic material is placed in a mold and then sintered to form the shell of the acetabular prosthesis. The bearing liner is formed by placing a polymer powder in the shell and through heat and pressure, is melted and formed into a solid bearing liner which interdigitates into the interior porous region of the shell of the acetabular prosthesis.

In a first embodiment, an acetabular prosthesis includes a rigid exterior shell that forms the acetabular cup and a bearing liner is formed and interdigitated on the inside, which include the regions that overlay the top edge of the cup.

In another embodiment, the bearing liner formed on the inside of the acetabular cup protrudes at an angle from the opening of the acetabular cup. In particular, the bearing liner would then allow the hip joint to have an angle which is different from the implantation angle of the acetabular cup.

In yet another embodiment, the bearing liner extends a distance above the outer edge of the ceramic portion of the acetabular cup. In particular, the bearing liner creates a wall along the edge of the acetabular cup in a specific arcuate region. The wall creates an arcuate region in which the hip bone would not be able to rotate within the prosthesis.

In yet another embodiment, the non-porous middle region of the acetabular cup extends through and creates an upper collar above and around the outer and inner porous regions. Further formed in the collar are holes or indents to accept an impacter instrument. The impacter instrument is used to align the acetabular prosthesis during the surgical procedure and hold the instrument in place while the acetabular prosthesis is impacted into the bone portion.

In yet another embodiment, an upper collar of non-porous material extends down and over the outer porous region to provide fins which help align the acetabular prosthesis when it is being implanted into the bone. The fins allow the acetabular prosthesis to be placed properly in the acetabulum to receive the ball of the femur to form the hip joint.

In yet another embodiment, non-porous material extends through the bottom of the acetabular cup. That is, portions of the non-porous material extend through the outer porous region to form spikes near the bottom of the acetabular cup. These spikes formed by the non-porous material help secure the acetabular prosthesis in its final implanted position. In this way, a minimum amount of cement or other holding materials may be necessary to ensure that the acetabular prosthesis is affixed in the proper position.

Further areas of applicability of the present invention will become apparent from the detailed description provided hereinafter. It should be understood that the detailed description and specific examples, while indicating the preferred embodiments of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION OF THE PREFERRED EMBODIMENTS

The following description of the embodiment(s) are merely exemplary in nature and are in no way intended to limit the invention, its application, or uses. Furthermore, while the present invention is described in association with an acetabular cup for a hip joint, those skilled in the art will appreciate that the present invention may be incorporated into various orthopedic implants for a human body such as knee, shoulder, and other joints. Therefore, it is to be understood that the present illustrative embodiments are not meant to limit the present invention.

Figure 1:
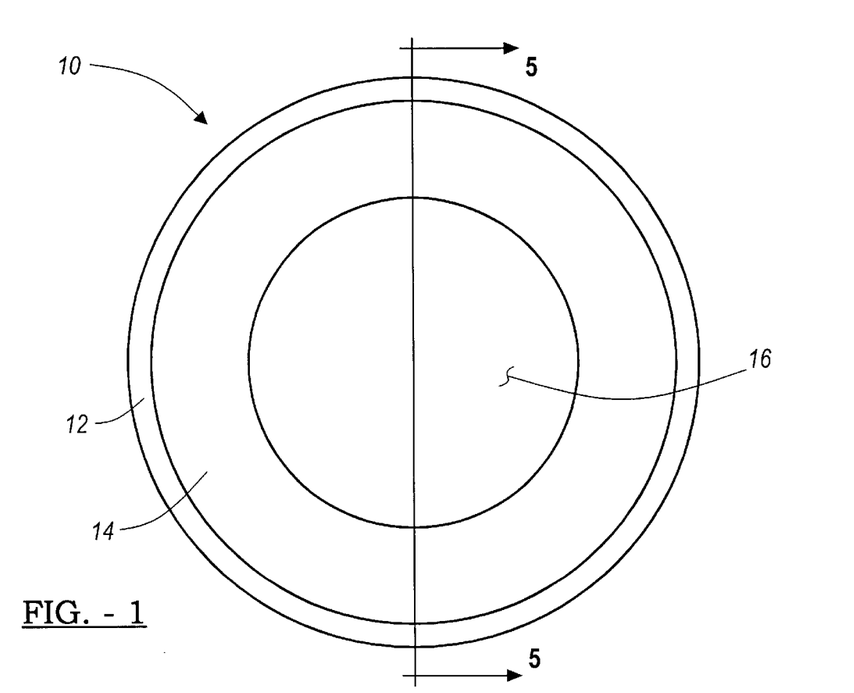
FIG. 1 is a top view of a non-modular acetabular cup according to a first embodiment of the present invention.
Figure 2:
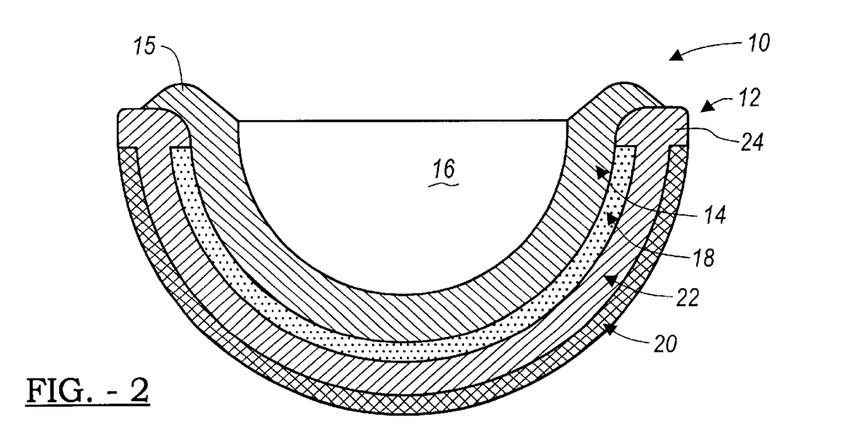
FIG. 2 is a cross-sectional view taken along line 2—2 of FIG. 1.

With reference to FIGS. 1 and 2, a first embodiment of the present invention is illustrated. An acetabular prosthesis is shown generally at 10. The acetabular prosthesis 10 includes two main portions: an outer shell component 12 and an inner liner or bearing 14 affixed to the interior of the shell 12. The liner 14 includes a hollow interior region 16 that forms the articulating surface which receives a natural or prosthetic femoral head. With particular reference to FIG. 2, the shell 12 generally includes three layers: an interior layer 18 that is porous and receives the liner 14 during formation, further described herein; an exterior porous layer 20 that forms the exterior of the shell 12 and engages the bone when implanted; and an intermediate non-porous layer 22 between the inner porous layer 18 and the outer porous layer 20. It will be understood that the shell 12 may take any shape necessary for the particular orthopedic prosthesis, as mentioned above. The hemispherical or cup shape illustrated is exemplary only for the acetabular prosthesis 10 embodiment. The inner porous layer 18 forms the interior of the shell 12 and the outer porous layer 20 extends generally around the entire perimeter of the hemisphere and both terminate at a generally equal meridian of the shell 12. However, the intermediate non-porous layer 22 extends and terminates at a different meridian above the meridian of the inner layer 18 and the outer layer 20. In this way, the upper region of the shell 12 includes an upper rim or collar 24 which is a hard region formed of the non-porous material from the non-porous region 22. This collar 24 helps in the implantation of the acetabular prosthesis 10, as described herein.

The entire shell 12 is formed into a single piece before the addition of the liner 14. If the shell 12 is formed of ceramic, the following is an exemplary process to form the shell 12. The ceramic which will become the non-porous region is first formed into a "green body" which is a compacted and molded ceramic powder. Once the "green body" is formed, the material which will become the porous layers is placed onto the inside and outside of the "green body." The three layers are then placed into a form. Then all the layers are sintered in the form to produce the final ceramic shell 12. The inner porous layer 18 and the outer porous layer 20 are formed during the sintering process. After sintering, however, each portion is integral with the others to form a firm ceramic shell 12. Although the ceramic shell 12 includes three layers, that being an inner layer 18, which is porous; an intermediate layer and an upper collar which is non-porous 22; and an outer layer 20 which is also porous, they are all integrally formed into one piece. It will also be understood that the shell 12 may be formed of other materials such as metal wherein the inner and outer surfaces of a metal shell may be made porous. Furthermore, other methods may be used to achieve similar ceramic formations not substantially different from the present invention.

Once the shell 12 is formed, then the liner 14 is integrated into the shell 12. In particular, a portion of a polymer powder is placed within the shell 12, which, after processing the powder, forms the liner 14. Preferably, the polymer powder is Ultra High Molecular Weight Polyethylene (UHMWPE). After the UHMWPE powder is placed into the interior of the shell 12, the entire system is placed into a molding apparatus. Briefly, the shell 12 is held in a lower plunger while an upper plunger presses down into the UHMWPE powder void 16 placed in the shell 12 and thereby forming the UHMWPE powder into the proper formation. Then the entire apparatus is heated to a suitable temperature to melt the UHMWPE powder. Pressure is also applied to the system to ensure that a proper formation of the liner 14 is created. As the UHMWPE powder melts, it flows into the pores created within the inner porous layer 18. The flow of the UHMWPE into the pores interdigitates the UHMWPE such that when the polymer is cooled and solidified, the interdigitated portion will hold the liner 14 in place within the shell 12. After a suitable time under the heat and pressure of the molding apparatus, the acetabular prosthesis 10 is removed and allowed to cool. The melted UHMWPE solidifies to form the liner 14 which includes liner collar regions 15 that extend above and on top of the non-porous collar 24. The liner 14 is held within the shell 12 by the portions of the polymer that have interdigitated into the inner porous region 18.

The acetabular prosthesis 10 may include an entirely non-modular formation. In particular, while the shell 12 includes several layers, the final product is completely integral and forms a seamless whole. Each of the layers are integral, making them unitary to substantially reduce or eliminate micromotion. Also the liner 14 interdigitates into the inner porous region 18, thereby integrating the liner 14 into the shell 12. The inner non-porous layer 22 also acts as a barrier to prevent the migration of the liner 14 through the shell 12. The pores in the outer porous layer 20 provide places for bone ingrowth once the acetabular prosthesis 10 is surgically implanted into the patient. Furthermore, it is to be understood that each region of the acetabular prosthesis 10 may be varied in thickness depending upon the particular patient or application necessary. Additionally, the shell 12 may include modular attachments to assist in implantation.

It is preferred that the inner porous region 18 has substantially all of its pores interdigitated by the liner 14. Depending on the polymer or other material being used, the thickness of the inner porous layer 18 may be adapted to ensure that substantially all of the pores formed in the inner porous layer 18 are interdigitated. In particular, it is preferred that the thickness of the inner porous layer 18 be in the range of about 0.3 mm to 2 mm. It is also understood that the outer porous layer 20 may be varied in thickness depending upon the amount of bone ingrowth anticipated within the particular patient. Furthermore, the porosity of the inner porous layer 18 and the outer porous layer 20 may be adapted depending upon the type of polymer being used in the polymer liner 14 or the amount of bone ingrowth anticipated in the patient. Preferably, porosities for the inner porous layer 18 is between about 40 and about 70 percent, and preferably about 50 to about 60 percent, while the porosities of the outer layer 20 is in the range of about 40 to about 70 percent, and preferably about 60 to about 70 percent. The overall porosity percentage of the shell 12 is in a range between about 10 percent to 47 percent. Additionally, the outer porous region 20 may be impregnated or covered with a bio-active material, preferably bio-active glass, to encourage bone ingrowth.

Figure 3:
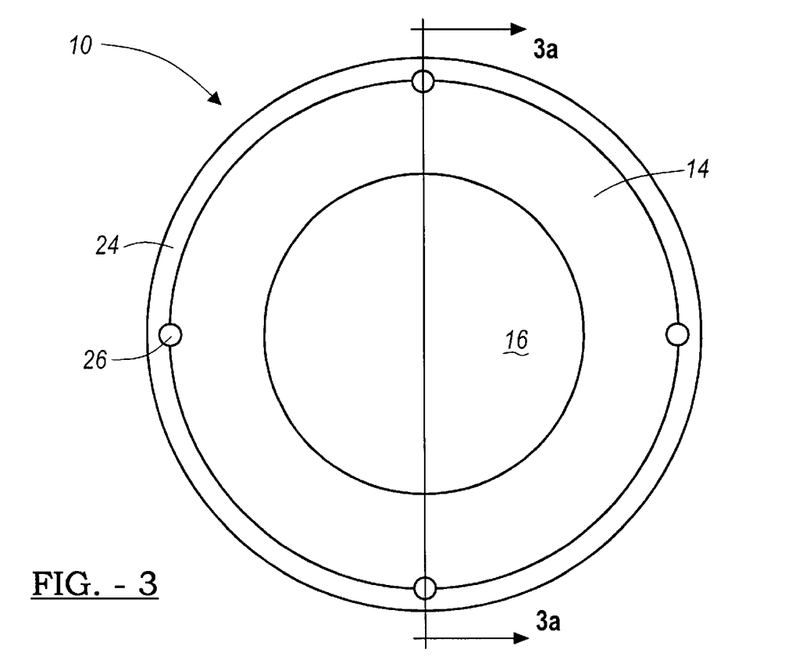
FIG. 3 is a plan view from the top of an acetabular cup including tool detents on the top thereof.
Figure 3A:
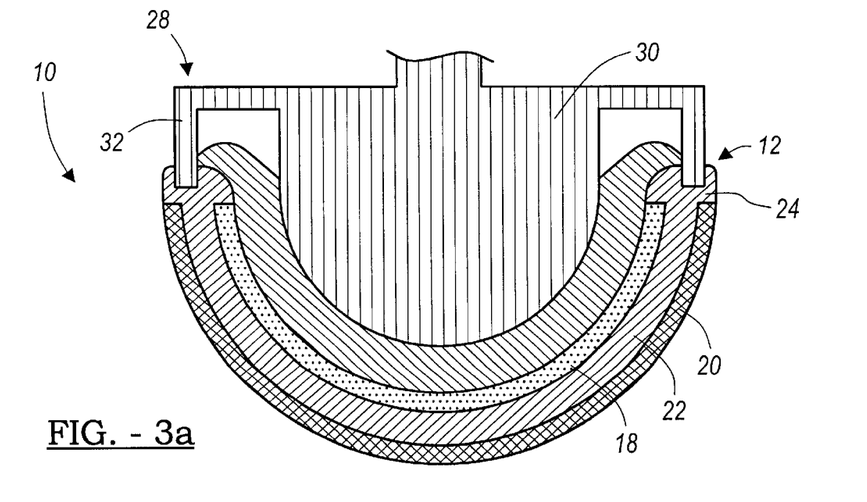
FIG. 3a is a cross-sectional view taken along lines 3—3 of FIG. 3.

With reference to FIGS. 3 and 3a, the acetabular prosthesis 10 of the first embodiment may include detents or bores 26 in the collar 24. The detents 26 help in the placement and positioning of an impacter or implantation tool 28, illustrated more fully in FIG. 9a. The impacter 28 includes a primary hemispherical head 30 which is complimentary to and inserted into the articulating region 16 of the acetabular prosthesis 10. Fingers or legs 32 extend from the head 30 and engage the detents 26. The legs 32 associate with the detents 26 to ensure that the impacter tool 28 is held steady and positioned properly for the implantation of the acetabular prosthesis 10. Furthermore, the fingers 32 assist in the rotational positioning of the acetabular prosthesis 10 during implantation. When the shell 12 is formed of a ceramic, the collar 24 is able to receive the force of the legs 32 of the impacter tool 28 due to the fact that it is formed of the non-porous ceramic. Once the acetabular prosthesis 10 is properly positioned using the tool 28, the acetabular prosthesis 10 is impacted into the bone of the patient undergoing the surgery, as is known in the art.

Figure 4:
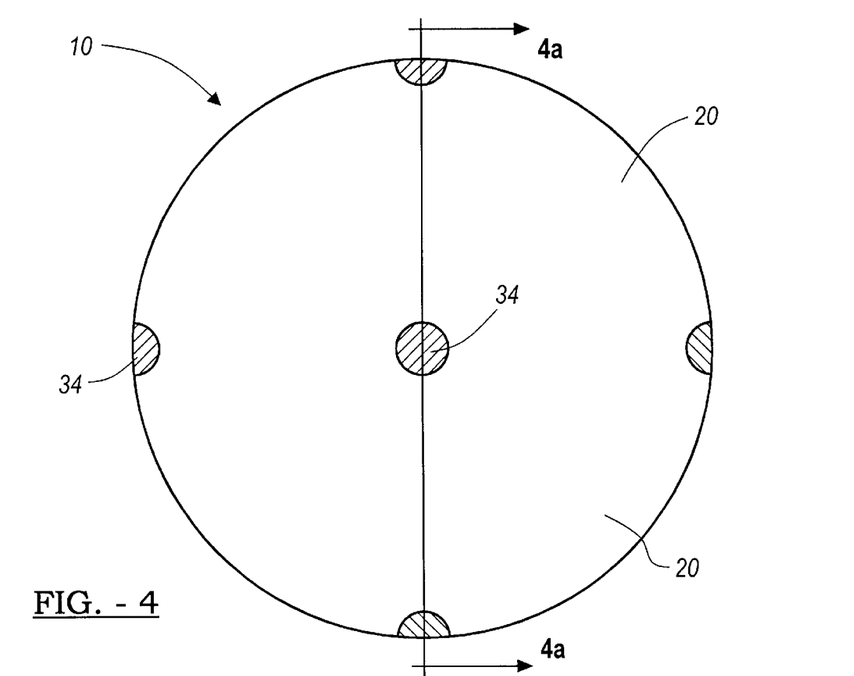
FIG. 4 is a plan view from the bottom of the acetabular cup including portions to assist in molding.
Figure 4A:
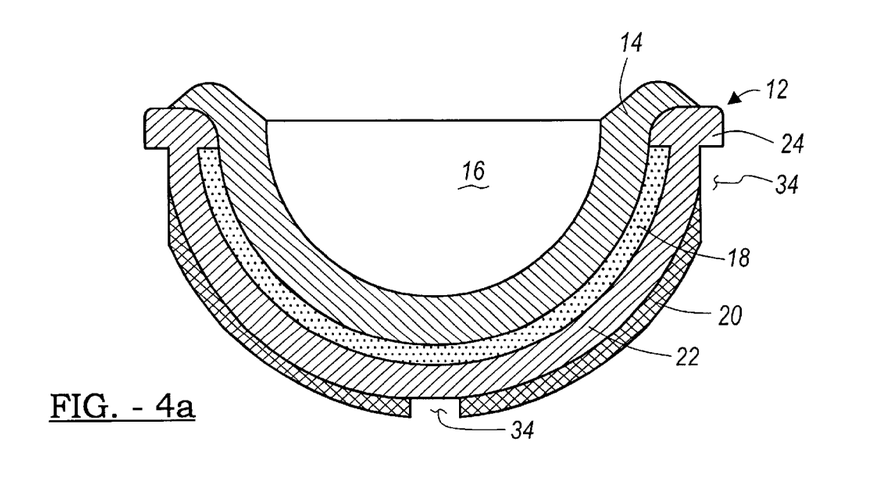
FIG. 4a is a cross-sectional view taken along lines 4a—4a of FIG. 4.

With reference to FIGS. 4 and 4a, voids 34 may be formed in the outer porous region 20 of the cup 12 to assist in the molding and affixation of the liner 14. That is, during the formation of the shell 12, certain voids 34 may be left in the outer porous region 20 to assist in the mounting of the shell 12 during the formation and affixation of the liner 14. In this way, the mounting portions or plungers of the apparatus to melt and form the liner 14 may engage the shell 12 without harming the outer porous region 20. Therefore, the acetabular cup 12 will retain its integrity during the molding of the liner 14. By creating the bores 34 in the outer porous region 20, increased pressure may be placed upon the shell 12 during the molding of the liner 14, since the plungers of the molding apparatus engage the non-porous layer 22. This allows for an additional control of the molding process of the liner 14 and ensures a proper interdigitation of the liner 14 into the inner porous region 18. The access to the non-porous region 22 are particularly helpful where the control of pressure or necessity of increased pressure exists.

Figure 5:
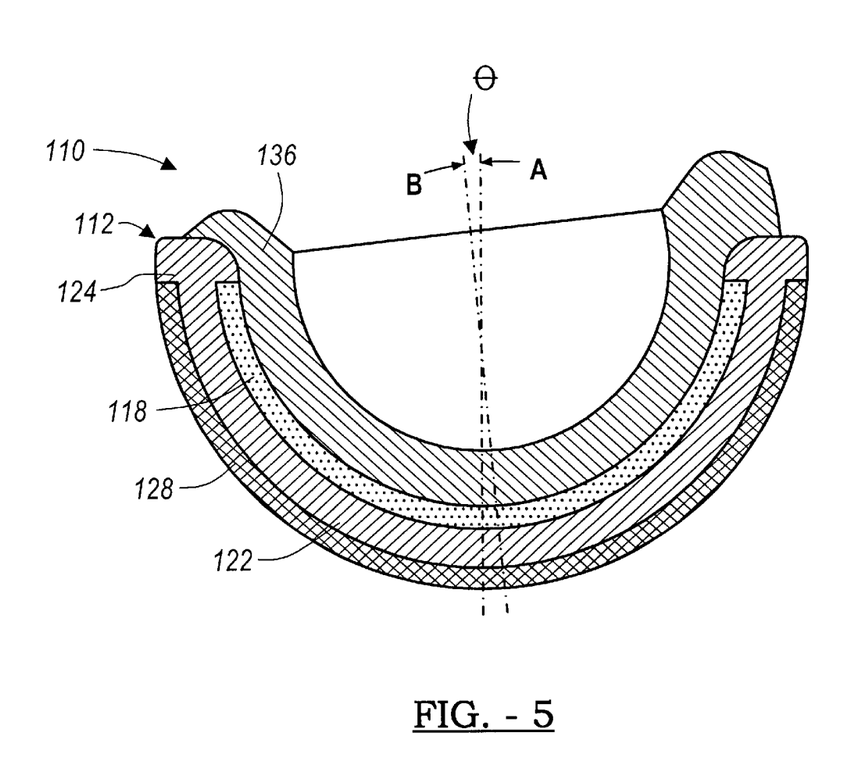
FIG. 5 is a cross-sectional view of a second embodiment of the present invention.

With reference to FIG. 5, a second embodiment of the present invention is illustrated where portions similar to the first embodiment of FIG. 1 are given like numerals increased by 100. The acetabular prosthesis 110 includes a shell 112 having an inner porous layer 118, an outer porous layer 120, and a non-porous layer 122 there between. Additionally, a non-porous collar 124 extends above the inner porous layer 118 and the outer porous layer 120 to form an upper meridian of non-porous material. A liner 136 is affixed to the shell 112 as explained above. However, according to the second embodiment, the center line A of the liner 136 is not parallel to the center line B of the shell 112. That being that the center line B of the hemisphere of the liner 136 is formed at an angle $\measuredangle$ a particular number of degrees from the center line A of the hemisphere of the shell 112. The angle $\measuredangle$ will depend upon the particular circumstances of the patient, the surrounding ilium, and other factors for a proper fit of the femur head in the acetabular prosthesis 110. This is used generally when the acetabular prosthesis 110 is inserted into a bone that is not in the proper alignment and cannot be repaired. Therefore, the liner 136 is tilted to properly accept and align the femoral prosthesis that is implanted into the hip joint.

The formation of the first embodiment of the acetabular prosthesis 10 as described above in relation to the first embodiment is the same in regard to the formation of the acetabular prosthesis 110 of the second embodiment. However, the molding of the liner 136 is modified only to ensure the proper placement of the liner 136 in its tilted orientation. It is also understood that the bores 26 and the voids 34 may be placed in the second embodiment to ensure proper placement and forming of the acetabular prosthesis 110. In particular, the voids 34 in the outer porous region 120 are advantageous to ensure that enough pressure in the right direction is placed onto the polymer powder which will be formed into the liner 136 to ensure the proper tilt in forming the liner 136.

Figure 6:
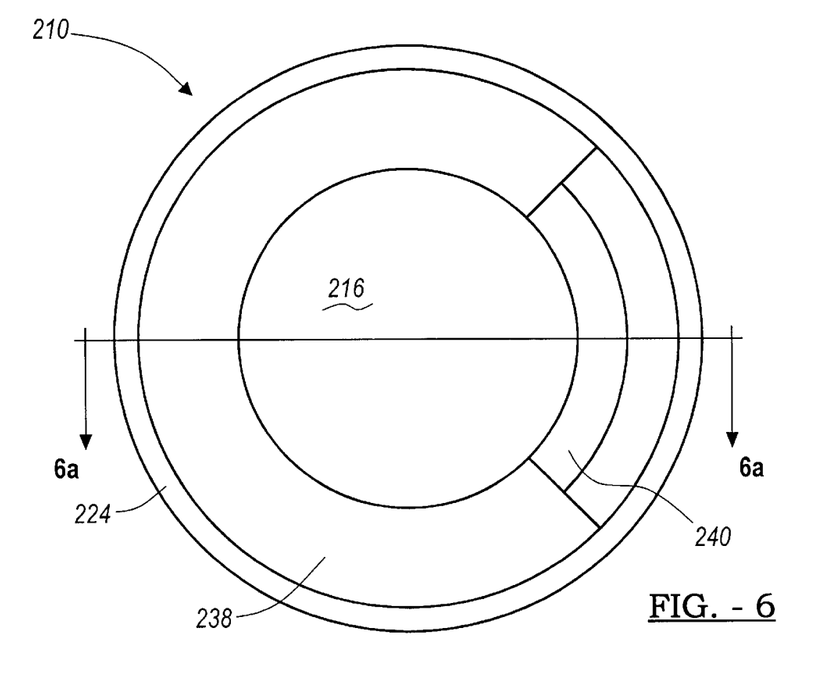
FIG. 6 is a plan view from the top of a third embodiment of the present invention.
Figure 6A:
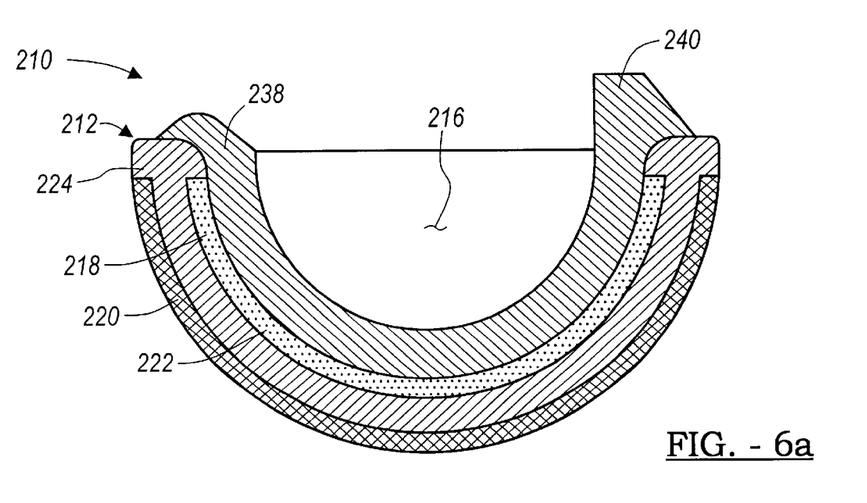
FIG. 6a is a cross-sectional view taken along line 6a—6a of FIG. 6.

With reference to FIGS. 6 and 6a, a third embodiment of the present invention is described where portions similar to the first embodiment have similar numerals increased by 200. The acetabular prosthesis 210 includes a ceramic cup 212 which has an inner porous layer 218, an outer porous layer 220, and an intermediate non-porous layer 222 in between. Additionally, a non-porous collar 224 creates an upper meridian on the top of the shell 212. Formed within the shell 212 and interdigitated into the inner porous region 218 is a liner 238. The liner 238 defines an inner articulating region 216 which receives the ball portion or femoral head of a hip joint. According to the third embodiment, one arc portion of the liner 238 forms a wall 240. The wall 240 ensures that the femoral head is not able to dislocate from the inner articulating region 216 of the bearing liner 238 during impingement of the femoral stem with the acetabular prosthesis 210. When the femur is allowed to move to extreme ranges of motion, the likelihood of dislocating the femoral head from the liner 238 increases. Therefore, the wall 240 increases the range needed to dislocate the femoral head thereby decreasing the likelihood of dislocations. The surgeon may place wall 240 at any position during implantation that the surgeon believes such an extreme range may occur.

Figure 7:
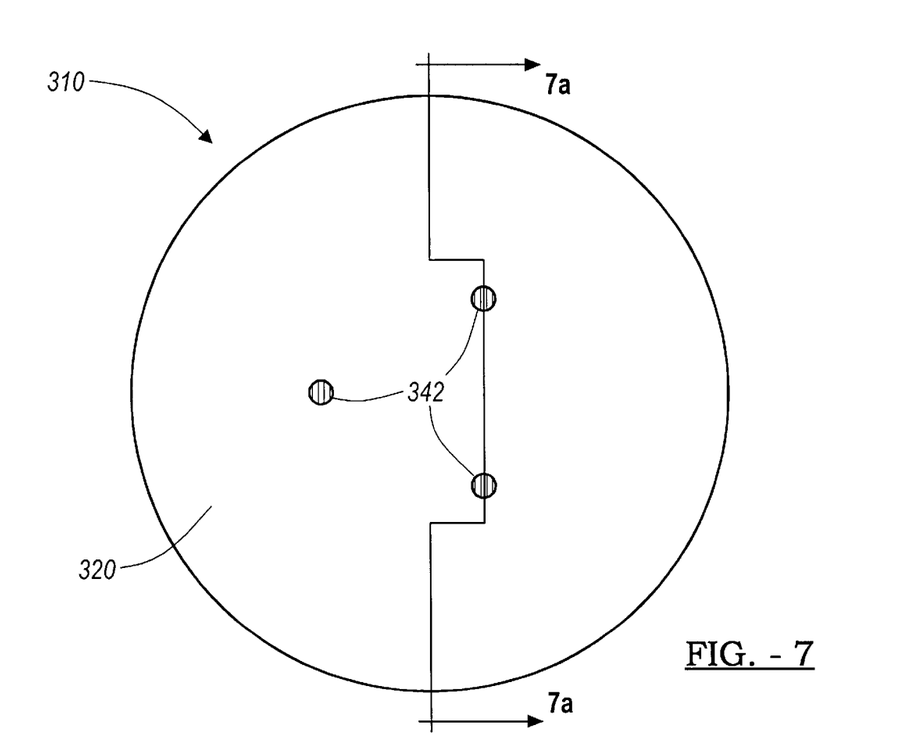
FIG. 7 is a plan view from the bottom of a fourth embodiment of an acetabular cup according to the present invention.
Figure 7A:
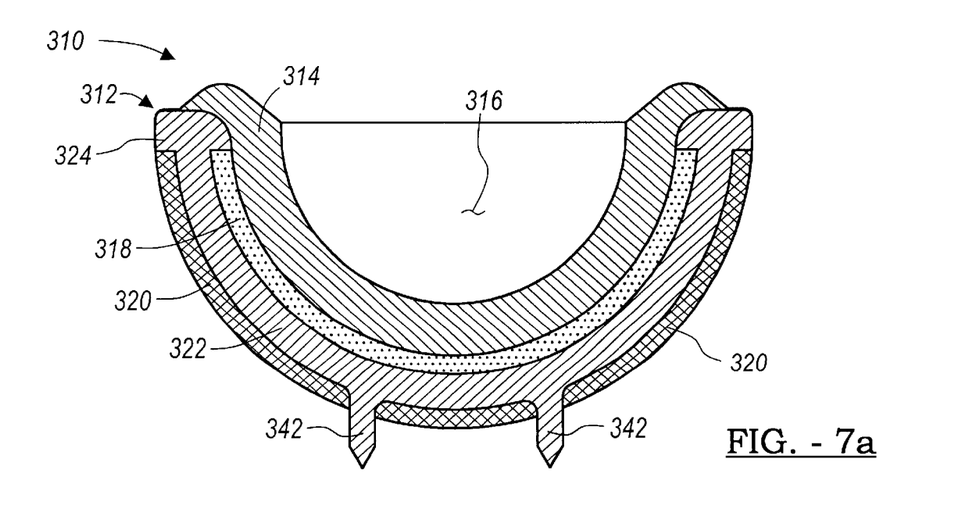
FIG. 7a is a cross-sectional view taken long line 7a—7a of FIG. 7.

With references to FIGS. 7 and 7a, a fourth embodiment of the present invention is illustrated where elements similar to the first embodiment have like numerals increased by 300. An acetabular prosthesis 310 includes a shell 312 which has an interior porous layer 318, an exterior porous layer 320, and a non-porous layer 322 therebetween. Additionally, a non-porous collar 324, integral with the inner non-porous region 322, forms an upper meridian of the shell 312. Formed within the hemispherical void of the shell 312 and interdigitated into the inner porous region 318 is a liner 314. Formed within the liner 314 is an articulating region 316 to receive the ball portion of the hip joint. According to the fourth embodiment, portions of the non-porous layer 322 form spikes 342 that extend down and through the outer porous layer 320. The spikes 342 are formed in the non-porous layer 322 during the initial formation process of the shell 312. In this way the spikes 342 are integral with the shell 312 thus forming a unitary cup 312. When the shell 312 is formed of ceramic during formation of the "green body," the spikes 342 are molded into the compacted ceramic powder.

The non-porous spikes 342 help assist in the implantation of the acetabular prosthesis 310 into the patient. It is to be understood that the acetabular prosthesis 310 may include detents similar to that described above (26 in FIG. 3). In this way when the acetabular prosthesis 310 is being implanted into the patient, the spikes 342 are driven into the bone of the acetabulum to help secure the acetabular prosthesis 310 in position. Additionally, the acetabular prosthesis 310 may include voids 34 to assist in formation of the shell 312 and spikes 342. The spikes 342 ensure that the implanted acetabular prosthesis 310 is not allowed any movement post operatively. Additionally, the spikes 342 assist in the fixation of the acetabular prosthesis 310 to the bone of the ileum.

Figure 8:
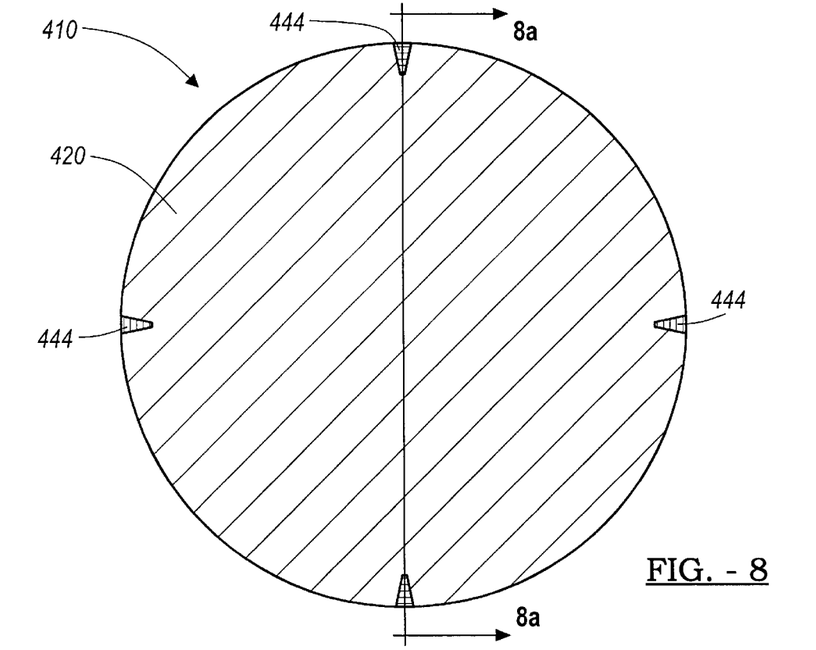
FIG. 8 is a plan view from the bottom of an acetabular cup according to a fourth embodiment of the present invention.
Figure 8A:
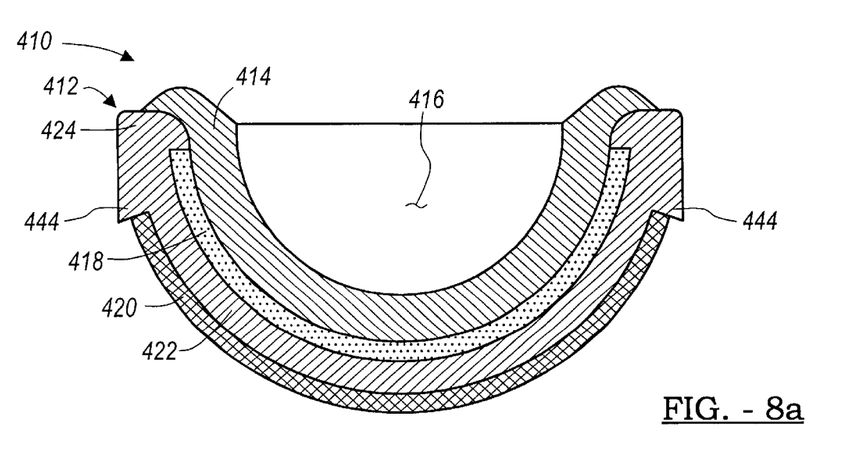
FIG. 8a is a cross-sectional view taken along line 8a—8a of FIG. 8.

With reference to FIGS. 8 and 8a, a fifth embodiment of the present invention is illustrated, where portions similar to those described according to the first embodiment have like numerals increased by 400. An acetabular prosthesis 410 includes a ceramic cup 412 which has an inner porous layer 418 and an outer porous layer 420 with a non-porous layer 422 therebetween. Formed within and interdigitated into the inner porous layer 418 is a liner 414 which defines the articulation region 416 which receives the ball portion of the hip joint. Additionally, a collar 424 of non-porous material forms the upper meridian of the shell 412.

At the upper meridian of the shell 412 are fins or protrusions 444 of non-porous material. In particular, the fins 444 are extensions of the collar 424 of the shell 412. Again, when the shell 412 is formed of ceramic, the fins 444 are formed during the sintering process of the non-porous ceramic powder. The fins 444 help position the acetabular prosthesis 410 in the acetabulum of the patient during the operative procedure. This helps ensure that proper alignment of the acetabular prosthesis 410 occurs during implantation. Additionally, the fins 444 assist the acetabular prosthesis 410 in maintaining its correct orientation within the patient after implantation and further prevents rotation of the acetabular prosthesis 410.

It is to be understood that each of the embodiments may include portions of the other embodiments as described above. That is each embodiment is not exclusive to itself. For example, the acetabular prosthesis 10 according to the first embodiment may also include the fins 444 as described in relation to the fourth embodiment to assist in the alignment of the acetabular prosthesis 10. Additionally, each of the embodiments may include the voids 34, as described in conjunction with the first embodiment, to help in the formation of the liner.

Figure 9:
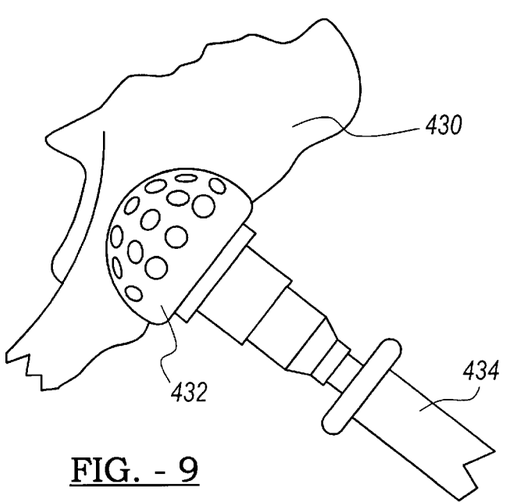
FIG. 9 is a plan view of an acetabulum and reamer to prepare an acetabulum for an acetabular prosthesis according to the present invention.
Figure 9A:
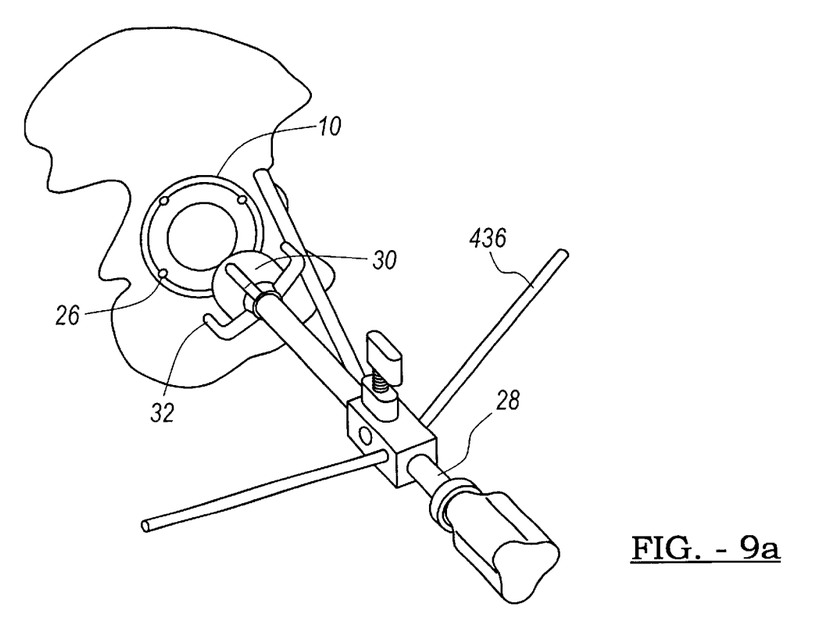
FIG. 9a is a perspective view of a tool implanting the prosthesis according to the present invention.

The method for implanting the acetabular prosthesis 10 will now be described with reference to FIGS. 9 and 9a. It will be understood that the method for implanting the other preferred embodiments of the acetabular prosthesis disclosed herein will also follow a similar procedure. It is also understood that the embodiments described above may be varied only slightly to create other orthopedic prosthesis such as knee, shoulder, wrist, hand, neck, or other joints, particularly any articulating joints. These variations, however, do not remove them from the breadth of the present invention.

It will be understood that while the acetabular prosthesis 10 disclosed herein are discussed in engaging the acetabulum or any region of the acetabulum, these components may engage just the acetabulum or any region of the acetabulum in the surrounding pelvis such as the ilium, pubis, and ischium or engaging the other bone anatomy of the patient. Once an x-ray has been taken of the hip or hip prosthesis that is to be replaced, a suitably sized acetabular prosthesis 10 is selected. Once the proper acetabular prosthesis 10 is chosen, a suitably sized hip prosthesis (shown in FIG. 10) to fit within the intramaduliary canal of a host femur is also chosen. The hip prosthesis may include many different types of hip prosthesis generally known in the art and available to physicians. Once all the proper prosthesis have been chosen, a surgical incision is made and the hip joint is dislocated to expose the acetabulum 430. The head of the femur may also be resected if a hip prosthesis is to be implanted into the femur.

Once the acetabulum 430 has been exposed, it may be necessary to remove degenerated bone, cartilage, or, if performing a revisionary prosthesis, the cement of the previous acetabular cup may need to be reamed out. In this case, a reamer 432 driven by a motor 434 is used to remove the degenerated bone cartilage or other material from the acetabulum 430. Furthermore, the reamer 432 insures that the acetabulum 430, which is to receive that acetabular prosthesis 10, is the proper form and shape to receive the acetabular prosthesis 10.

Once the acetabulum 430 has been prepared by the reamer 432, the acetabular prosthesis 10 is implanted. The acetabular prosthesis 10 may include bores 26 to position the tool and provide additional support for impacting the acetabular prosthesis 10 into the acetabulum 430. Additionally the impacter 28 may include one or more guide legs 436 which engage the pelvis or other landmarks of the patient to insure proper alignment of the impacter 28 and thereby of the acetabular prosthesis 10. Once the proper alignment is determined and checked using the guide legs 436, the impacter tool 28 is driven down into the acetabular prosthesis 10 thereby setting the acetabular prosthesis 10 into the acetabulum 430. Once the acetabular prosthesis 10 is impacted into the acetabulum 430, it is held in place by friction or other cementing materials which were placed in the acetabulum 430 after being prepared by the reamer 432.

Figure 10:
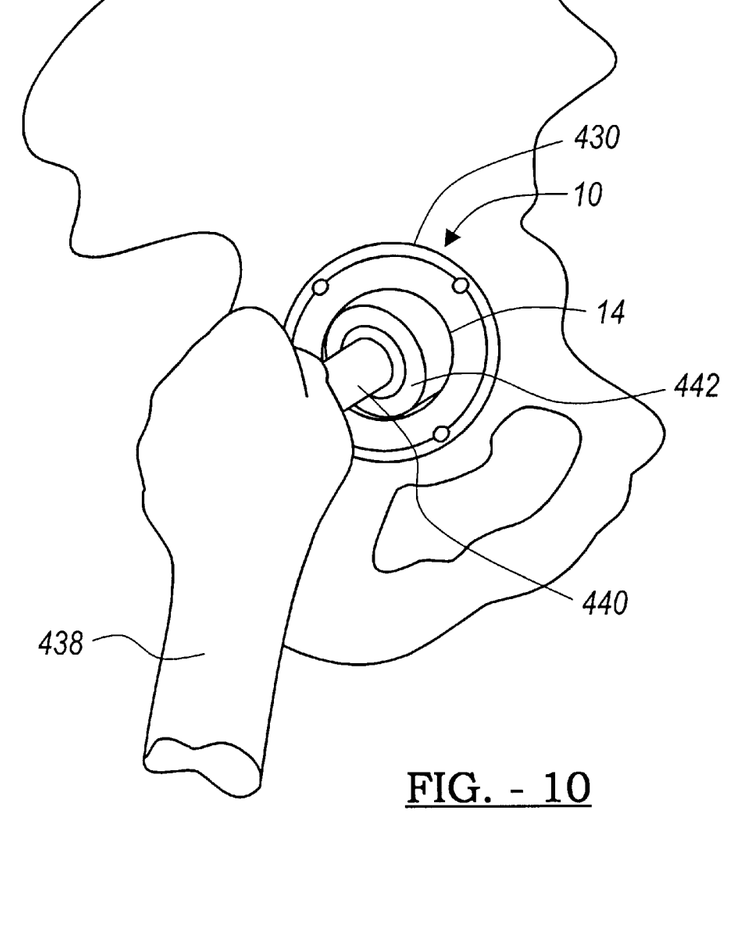
FIG. 10 is a perspective view of an implanted acetabular prosthesis according to the present invention with a hip prosthesis associated therewith.

With reference to FIG. 10, a fully implanted acetabular prosthesis 10 is shown implanted into the acetabulum 430. Additionally, a femur 438 is shown to include a hip prosthesis 440 which when returned to the acetabulum 430 includes a ball joint 442 which rides within the liner 14 of the acetabular prosthesis 10. It is understood that the head 442 of the hip prosthesis 440 rides within the liner 14 of the acetabular prosthesis 10.

The non-porous region of the present invention provides an impenetrable barrier to foreign materials. In particular, after implantation of the acetabular prosthesis according to the present invention, foreign materials would not be able to flow into the acetabular prosthesis. Additionally, since the inner liner is interdigitated into the shell, no internal motion may occur of the liner. Therefore, the liner does not wear as quickly as a liner which is not held as firmly in place. In particular, the liner is affixed to the inner porous region of the shell through hundreds of digits which have interdigitated into the pores. Since this is the case, the liner is held in place at nearly every point along the interface with the inner porous region. Additionally, since the liner is not allowed to move, there is also less of a chance that foreign material would make its way into the acetabular prosthesis post operatively. Therefore, wear is reduced and integrity of the prosthesis is heightened. It is to be understood, however, that any porous substance may achieve these results. As an example, a shell formed of titanium may have pores formed into it which would allow interdigitation of the liner.

The description of the invention is merely exemplary in nature and, thus, variations that do not depart from the gist of the invention are intended to be within the scope of the invention. Such variations are not to be regarded as a departure from the spirit and scope of the invention.

What is claimed is:

1. An orthopedic prosthesis for implantation into a bone of a patient, said orthopedic prosthesis comprising:
    a ceramic shell having at least an inner porous ceramic layer, an intermediate substantially non-porous ceramic layer, and an outer porous ceramic layer; and
    a bearing liner having a first side and a second side;
    wherein said first side is affixed to said inner porous ceramic layer;
    wherein said second side is an articulation surface;
    wherein said ceramic shell is adapted to be affixed within the bone and said outer porous ceramic layer is adapted to receive bone ingrowth after the implantation.

2. The orthopedic prosthesis of claim 1, wherein said ceramic shell generally defines a hemisphere and an upper meridian of said hemisphere is defined by a non-porous ceramic collar.

3. The orthopedic prosthesis of claim 2, wherein said shell is unitarily formed such that each of said layers are integral with an adjacent layer.

4. The orthopedic prosthesis of claim 3, wherein said bearing liner is affixed to said inner porous ceramic layer by interdigitation of substantially all the outer perimeter of said bearing liner into the pores of said inner porous ceramic layer such that said bearing liner and said inner porous ceramic layer are integral components.

5. The orthopedic prosthesis of claim 2, wherein said non-porous ceramic collar includes a plurality of detents;
    wherein said detents allow a tool to engage non-porous ceramic.

6. The orthopedic prosthesis of claim 2, wherein said collar includes fins protruding from said collar.

7. The orthopedic prosthesis of claim 2, wherein said bearing liner forms a wall in an arcuate region above said collar.

8. The orthopedic prosthesis of claim 1, wherein said porosity and thickness of the inner layer and the outer layer are substantially the same.

9. The orthopedic prosthesis of claim 1, wherein said outer porous layer includes bores such that said intermediate substantially non-porous layer may be accessed through said bores.

10. The orthopedic prosthesis of claim 1, wherein said outer layer includes bores with a portion of said intermediate substantially non-porous layer extending therethrough.

11. The orthopedic prosthesis of claim 10, wherein said portion of said intermediate substantially non-porous layer terminates in a point to form a fixation spike.

12. The orthopedic prosthesis of claim 1, wherein said outer layer further comprises a bio-active material wherein said bio-active material stimulates bone growth.

13. The orthopedic prosthesis of claim 1, wherein each of said layers of said shell are made of a ceramic material.

14. The orthopedic prosthesis of claim 1, wherein said bearing liner is formed of an ultra high molecular weight polyethylene.

15. An acetabular prosthesis for implantation in an acetabulum and surrounding pelvis, said acetabular prosthesis comprising:
    an integrally formed shell having a first porous layer and a substantially non-porous second layer adjacent said first layer;
    a bearing liner integrally formed with said porous layer such that said liner is interdigitated into said porous layer;
    said bearing liner including a first side and a second side;
    said first side substantially affixed to said first porous layer;
    said second side forming an articulation surface;
    said shell adapted to be affixed within said acetabulum; and
    wherein each of said layers is formed of a ceramic.

16. The acetabular prosthesis of claim 15, wherein a third porous layer adjacent said second layer is adapted to receive bone ingrowth from the acetabulum.

17. The acetabular prosthesis of claim 16, wherein said second layer extends a distance beyond a meridian formed by said first layer and said third layer to form a non-porous collar at a second meridian.

18. The acetabular prosthesis of claim 17, wherein said collar defines a tool engaging detent to receive a portion of an implantation tool.

19. The acetabular prosthesis of claim 17, wherein said bearing liner includes a region that extends over the collar.

20. The acetabular prosthesis of claim 17, wherein said bearing liner forms a wall in a particular arc which extends above the collar.

21. The acetabular prosthesis of claim 16, wherein said bearing liner a includes polymer that is molded to said first layer and includes a portion interdigitated into said first layer.

22. The acetabular prosthesis of claim 21, wherein said bearing liner includes an articulation surface formed substantially of said polymer.

23. The acetabular prosthesis of claim 16, wherein a potion of said second layer extends through said third layer to assist in the said implantation of said acetabular prosthesis.

24. The acetabular prosthesis of claim 23, wherein said portion terminates in a point to form a spike of material from said second layer.

25. An orthopedic prosthesis to replace a hip joint comprising:
    an acetabular prosthesis having a shell formed of a plurality of integrated ceramic layers;

a bearing liner having a first side and a second side, said first side interdigitated into a first of said plurality of ceramic layers of said shell; and a femoral head prosthesis which articulates within said bearing liner and is affixed into the intramedullary region of a femur;

wherein said second side of said bearing liner is a surface that articulates with said femoral head.

26. The orthopedic prosthesis of claim 25, wherein said shell is adapted to be affixed within an acetabulum.

27. The orthopedic prosthesis of claim 25, wherein said bearing liner is formed in contact with said first porous layer to become said interdigitated.

28. The orthopedic prosthesis of claim 27, herein said second porous layer is adapted to receive bone ingrowth after implantation into a patient.

29. The orthopedic prosthesis of claim 28, wherein a portion of said substantially non-porous layer extends through said second porous layer to form spikes on the outside of said shell.

30. The orthopedic prosthesis of claim 25, further comprising:

a collar defined by at least one of said plurality of integrated ceramic layers.

31. The orthopedic prosthesis of claim 30, wherein said collar operably engages a tool for at least one of positioning and implantation of said shell.

32. An orthopedic implant for implantation into a body, wherein said orthopedic implant comprises:

a substantially ceramic shell comprising a first porous layer and a non-porous layer;

a liner, formed substantially of a polymer affixed to said first porous layer, to provide a substantially friction-free articulation surface;

a second porous layer extending from said non-porous layer; and said shell adapted to be received within the body.

33. The orthopedic implant of claim 32, wherein said non-porous layer is between said first porous layer and said second porous layer.

34. The orthopedic implant of claim 32, wherein the said substantially polymer liner is interdigitated into said first porous layer of said shell.

35. The orthopedic implant of claim 34, wherein said substantially polymer liner is interdigitated into said first porous layer by:

disposing a polymer mass adjacent said first porous layer;

melting said polymer mass such that a portion of said mass flows into a pore of said first porous layer.

36. The orthopedic implant of claim 32, wherein said non-porous layer includes spikes extending from said non-porous layer away from said first porous layer.

37. The orthopedic implants of claim 32, wherein said non-porous layer extends beyond said first porous layer and includes detents to receive an implantation tool.

38. The orthopedic implant of claim 32, wherein said shell is permanently affixed to the body through bone ingrowth into said second non-porous layer.

* * * * *

UNITED STATES PATENT AND TRADEMARK OFFICE
CERTIFICATE OF CORRECTION

PATENT NO. : 6,682,567 B1
DATED : January 27, 2004
INVENTOR(S) : David Wayne Schroeder It is certified that error appears in the above-identified patent and that said Letters Patent is hereby corrected as shown below:

Column 10,
Line 51, delete "a"
Line 58, "potion" should be -- portion --.

Column 11,
Line 14, "herein" should be -- wherein --.

Column 12,
Line 25, "implants" should be -- implant --.

Signed and Sealed this

Eleventh Day of January, 2005

JON W. DUDAS
*Director of the United States Patent and Trademark Office*